(12) United States Patent
Plemmons et al.

(10) Patent No.: US 7,280,200 B2
(45) Date of Patent: Oct. 9, 2007

(54) DETECTION OF A WAFER EDGE USING COLLIMATED LIGHT

(75) Inventors: Mark P. Plemmons, McKinney, TX (US); Timothy R. Tiemeyer, Randolph, MA (US)

(73) Assignee: ADE Corporation, Westwood, MA (US)

( * ) Notice: Subject to any disclaimer, the term of this patent is extended or adjusted under 35 U.S.C. 154(b) by 278 days.

(21) Appl. No.: 10/891,835

(22) Filed: Jul. 15, 2004

(65) Prior Publication Data

US 2005/0024632 A1    Feb. 3, 2005

Related U.S. Application Data

(60) Provisional application No. 60/488,364, filed on Jul. 18, 2003.

(51) Int. Cl.
*G01N 21/00* (2006.01)
*G01N 21/95* (2006.01)
*G01B 11/24* (2006.01)
*G01B 11/30* (2006.01)

(52) U.S. Cl. .............. 356/237.3; 356/612; 356/620; 250/559.42; 250/559.44; 250/559.45; 250/559.36; 250/559.06

(58) Field of Classification Search ............ 356/237.1, 356/237.2, 237.3, 612, 613, 615, 620; 250/559.01, 250/559.04, 559.06, 559.36, 559.4–559.45
See application file for complete search history.

(56) References Cited

U.S. PATENT DOCUMENTS

| | | | | |
|---|---|---|---|---|
| 4,862,121 A | * | 8/1989 | Hochschild et al. ........ 333/173 |
| 5,452,078 A | * | 9/1995 | Cheng ........................ 356/150 |
| 5,546,179 A | * | 8/1996 | Cheng ........................ 356/73 |
| 5,592,295 A | | 1/1997 | Stanton et al. .............. 356/426 |
| 5,712,701 A | * | 1/1998 | Clementi et al. ......... 356/237.2 |
| 6,088,092 A | * | 7/2000 | Chen et al. .............. 356/237.2 |
| 6,107,637 A | * | 8/2000 | Watanabe et al. ........ 250/559.3 |
| 6,201,601 B1 | * | 3/2001 | Vaez-Iravani et al. ... 356/237.4 |
| 6,249,342 B1 | * | 6/2001 | Cheng ..................... 356/237.2 |
| 6,252,242 B1 | * | 6/2001 | Brunfeld et al. ....... 250/559.45 |
| 6,256,092 B1 | * | 7/2001 | Tomita et al. ........... 356/237.1 |
| 6,262,432 B1 | * | 7/2001 | Brunfeld et al. ....... 250/559.45 |
| 6,459,807 B1 | * | 10/2002 | Guest et al. ................. 382/145 |
| 6,501,545 B2 | * | 12/2002 | Komuro et al. .......... 356/237.2 |
| 6,608,676 B1 | * | 8/2003 | Zhao et al. .............. 356/237.2 |
| 6,768,542 B2 | * | 7/2004 | Ise et al. ................. 356/237.2 |
| 6,798,503 B2 | * | 9/2004 | Hiramoto et al. ........ 356/237.1 |
| 7,046,837 B2 | * | 5/2006 | Guest et al. ................. 382/145 |

(Continued)

*Primary Examiner*—Gregory J. Toatley, Jr.
*Assistant Examiner*—Bryan J Giglio
(74) *Attorney, Agent, or Firm*—Weingarten, Schurgin, Gagnebin & Lebovici LLP

(57) ABSTRACT

A system and method of inspecting a semiconductor wafer that may be employed to detect and to characterize defects occurring on an edge of the wafer. The wafer inspection system includes an optical module for providing a light source to scan the wafer edge, a light channel detector for detecting light reflected from the wafer edge, and a processor and memory for converting detected signals to digital form, and for filtering and processing the digital data. The module includes a wafer edge scanning mechanism for projecting a collimated laser beam toward the wafer edge at a predetermined angle of incidence to scan the wafer edge for defects. The light channel detector detects light reflected from the wafer edge to obtain wafer edge data, which are applied to thresholds to determine the location of defects in the wafer edge.

37 Claims, 11 Drawing Sheets

U.S. PATENT DOCUMENTS

| | | |
|---|---|---|
| 7,110,106 B2 * | 9/2006 | Xu et al. .................. 356/237.5 |
| 2002/0024659 A1 * | 2/2002 | Tanaka .................... 356/237.2 |
| 2002/0179867 A1 * | 12/2002 | Fielden et al. ......... 250/559.45 |
| 2004/0012775 A1 * | 1/2004 | Kinney et al. ........... 356/237.2 |
| 2004/0246476 A1 * | 12/2004 | Bevis et al. ............. 356/237.5 |
| 2005/0023491 A1 * | 2/2005 | Young et al. .......... 250/559.42 |

* cited by examiner

DETECTION OF A WAFER EDGE USING COLLIMATED LIGHT

CROSS REFERENCE TO RELATED APPLICATIONS

This application claims priority of U.S. Provisional Patent Application No. 60/488,364 filed Jul. 18, 2003 entitled DETECTION OF A WAFER EDGE USING COLLIMATED LIGHT.

STATEMENT REGARDING FEDERALLY SPONSORED RESEARCH OR DEVELOPMENT

N/A

BACKGROUND OF THE INVENTION

The present application relates generally to systems and methods of inspecting semiconductor wafers, and more specifically to semiconductor wafer inspection systems capable of detecting and characterizing wafer edge defects.

Systems and methods of inspecting semiconductor wafers have traditionally been employed to detect defects occurring on a surface of a semiconductor wafer. For example, conventional laser-based surface scanning inspection systems may operate to detect localized light scatters on a semiconductor wafer surface. Such localized light scatters may be indicative of surface defects that may render one or more integrated circuits fabricated on the wafer surface to be non-functional. Conventional surface scanning inspection systems are typically configured to inspect a wafer surface within a given edge exclusion due to optical artifacts that may result from the edge of the wafer. This limitation of conventional surface scanning inspection systems has generally not impacted the utility of these systems since integrated circuits are normally not fabricated near the wafer edge.

However, even though integrated circuits are not normally fabricated near or on the edge of a semiconductor wafer, it has become increasingly important to detect and to characterize edge defects during semiconductor wafer processing. This is because wafer edge defects often produce flakes of wafer material that may contaminate portions of the wafer on which integrated circuits are subsequently fabricated. Further, mechanical stresses may increase during thermal processing of the wafer, resulting in the formation of cracks in the vicinity of the edge defects. Moreover, an edge defect such as a chip on the wafer edge may compromise the structural integrity of the wafer, allowing cracks to form and subsequently propagate through the bulk wafer material. Such cracks may propagate through one or more integrated circuits fabricated on the wafer, rendering the circuits useless. In addition, because edge defects may compromise the structural integrity of the wafer, the wafer may shatter within a wafer processing chamber, thereby resulting in the loss of the integrated circuits fabricated on the wafer and significant downtime while the processing chamber undergoes re-commissioning.

It would therefore be desirable to have a system and method of inspecting a semiconductor wafer that may be used to detect and to characterize defects occurring on the edge of the wafer. Such a semiconductor wafer inspection system and method would be capable of detecting and characterizing defects in the wafer edge that occur near the wafer surface.

BRIEF SUMMARY OF THE INVENTION

In accordance with the present invention, a system and method of inspecting a semiconductor wafer are provided that may be employed to detect and to characterize defects occurring on an edge of the wafer. In the presently disclosed embodiment, the semiconductor wafer inspection system comprises an optical module for providing a source of light to scan an edge of a semiconductor wafer, a light channel detector for detecting light reflected from the wafer edge, and at least one data processor and associated memory operative to convert detected signals to digital form and to execute stored algorithms for filtering and processing the digital data. The light channel detector may operate by detecting changes in the intensity of the reflected light, or by detecting deflections of the reflected light.

In one embodiment, the optical module includes a wafer edge scanning mechanism such as an acousto-optic deflector configured to project a collimated beam of laser light toward the wafer edge at a predetermined oblique angle of incidence to scan the wafer edge for defects. Further, the light channel detector includes a quadcell photodetector configured to detect variations in the intensity of the light reflected from the wafer edge during the edge scan. First, data representative of the wafer edge are assembled and filtered. A baseline is then established for the edge data set using a suitable least squares fit (LSF) or re-zeroing technique. Next, radial and tangential thresholds for edge deviations are defined based on a predetermined permissible amount of variation between each datum and the baseline. The entire wafer edge is then scanned, and light reflected from the wafer is detected to determine the intensity loss. Next, wafer edge data are collected based on the determined light intensity losses. The wafer edge data are then compared to the thresholds. Next, deviations in the edge data (i.e., over-threshold events) are flagged. Over-threshold flagged events are then detected and located on the wafer edge. In the event the data set exceeds the tangential threshold, the data are flagged as an edge defect.

Other features, functions, and aspects of the invention will be evident from the Detailed Description of the Invention that follows.

BRIEF DESCRIPTION OF THE SEVERAL VIEWS OF THE DRAWINGS

The invention will be more fully understood with reference to the following Detailed Description of the Invention in conjunction with the drawings of which.

DETAILED DESCRIPTION OF THE INVENTION

U.S. Provisional Patent Application No. 60/488,364 filed Jul. 18, 2003 entitled DETECTION OF A WAFER EDGE USING COLLIMATED LIGHT is incorporated herein by reference.

A system and method of inspecting a semiconductor wafer are disclosed for use in detecting and in characterizing defects that occur on an edge of the wafer. The presently disclosed wafer inspection system is particularly suited for detecting and for characterizing edge defects that occur between the polished wafer surface and the crown of the wafer edge.

Figure 1:
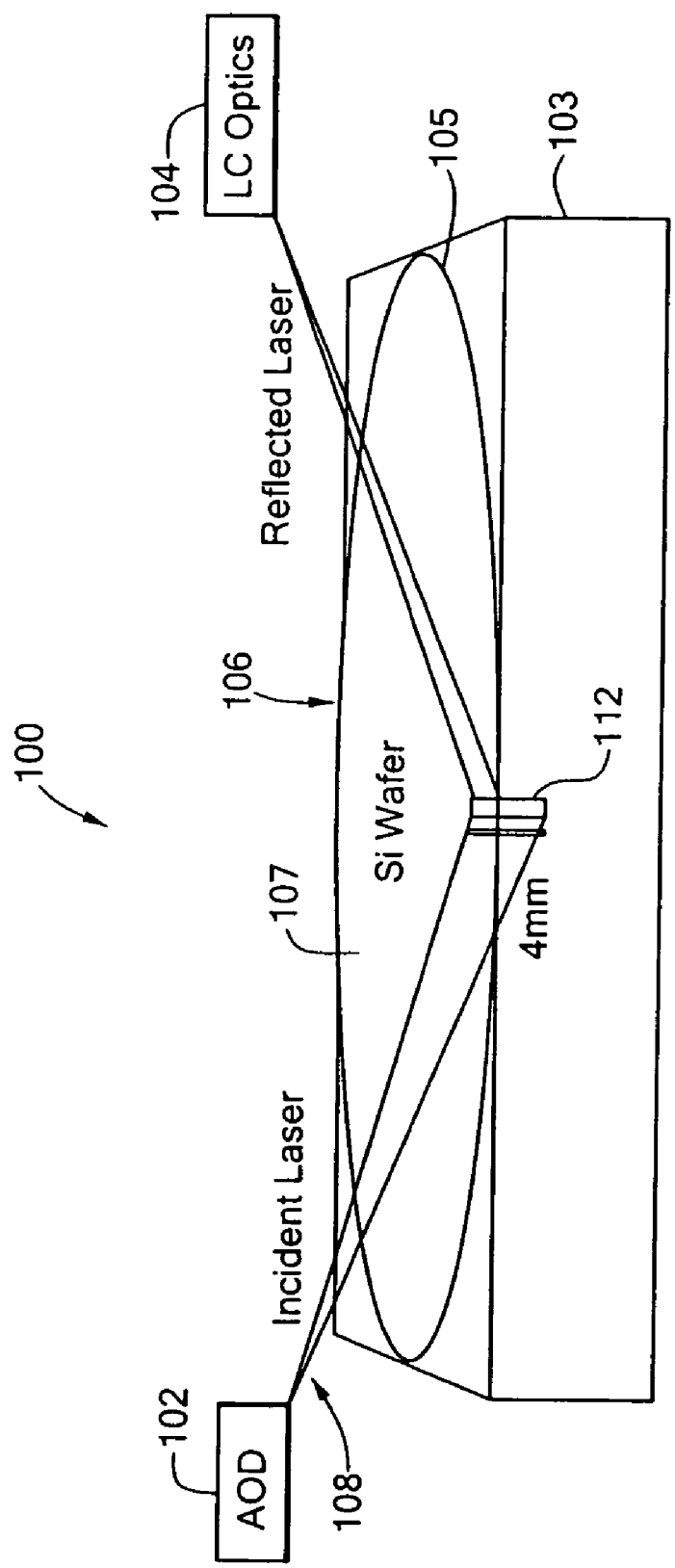
FIG. 1 is a diagram of a semiconductor wafer inspection system according to the present invention, in which the wafer inspection system performs a scan of a laser beam centered on an edge of a semiconductor wafer to detect edge defects.

FIG. 1 depicts an illustrative embodiment of a semiconductor wafer edge scanning inspection system 100, in accordance with the present invention. In the illustrated embodiment, the wafer inspection system 100 comprises an optical module including a wafer edge scanning mechanism 102, and a light channel (LC) detector including LC optics 104. For example, the wafer edge scanning mechanism 102 may be an acousto-optic deflector (AOD) or any other suitable scanning mechanism, and the LC optics 102 may comprise a quadcell photodetector or any other suitable light detector. As shown in FIG. 1, the AOD 102 is configured to project at least one collimated beam of laser light 108 toward an edge 105 of a semiconductor wafer 106 at an oblique angle of incidence θi (see also FIG. 16). Further, the LC optics 104 is configured to detect a light beam 110 specularly reflected from the wafer edge and/or a portion of the wafer surface 107 adjacent thereto. Specifically, the LC optics 104 is configured to detect specular distortions in the reflected light beam 110. It is noted that the wafer 106 may be inspected from the backside by inverting the wafer in the wafer inspection system 100.

For example, the AOD 102 may include a solid state laser such as a 532 nm wavelength diode-pulsed solid state laser, or any other suitable type of laser. In the preferred embodiment, the AOD 102 projects the laser light beam 108 to produce a focused laser spot having a diameter of about 30 microns for scanning the wafer edge 105, in which the incident angle θi of the projected light beam 108 is about 65 degrees. It should be understood that in alternative embodiments, the laser light beam 108 may be projected by the AOD 102 at any suitable angle of incidence. The wafer inspection system 100 also includes a theta (θ) stage 103 upon which the wafer 106 is held during inspection. In the preferred embodiment, the theta stage 103 is configured to rotate and to translate the wafer 106 through a scan line 112 of about 4 mm produced by the AOD 102, thereby generating a spiral pattern of light used to inspect the wafer edge 105. The theta stage 103 includes an encoder such as an optical encoder that provides counts indicative of the rotational position of the stage 103 relative to a predetermined reference point.

Figure 2:
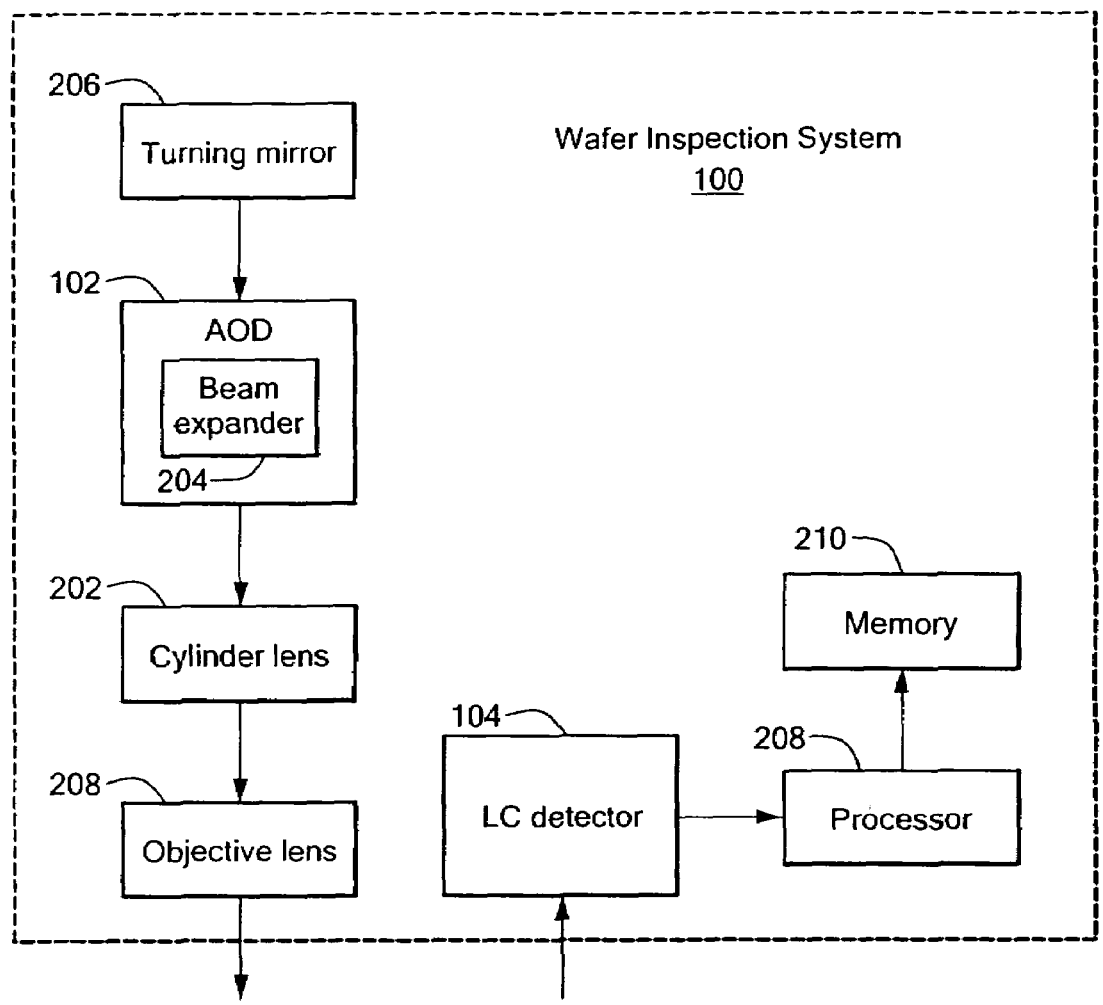
FIG. 2 is a functional illustration of the components used in the wafer inspection system of FIG. 1.

FIG. 2 depicts a plurality of functional components included in the above-described wafer inspection system 100 (see FIG. 1). As shown in FIG. 2, the system 100 comprises a turning mirror 206, the AOD 102 including a beam expander 204, a cylinder lens 202, an objective lens 208, the LC optics 104, and a processor 208 and associated memory 210. In the illustrated embodiment, the AOD 102 is configured to generate the narrow angle light beam 108 by exciting a crystal with a high frequency sound wave. The beam expander 204 is configured to expand the light beam 108 before the beam enters an aperture of the AOD 102 to obtain the desired angle of deflection. The cylinder lens 202 is disposed at the output of the AOD 102, and is configured to compensate for parasitic cylinder lens loss that may be induced by the deflector. The 4 mm scan is relayed through the objective lens 208 to the edge 105 and/or the adjacent surface of the wafer 106 (see also FIG. 1). The LC optics 104 is configured to receive the reflected light beam 110, and to detect any losses in light intensity resulting from specular distortion or deflection of the light beam 110.

Figure 10A:
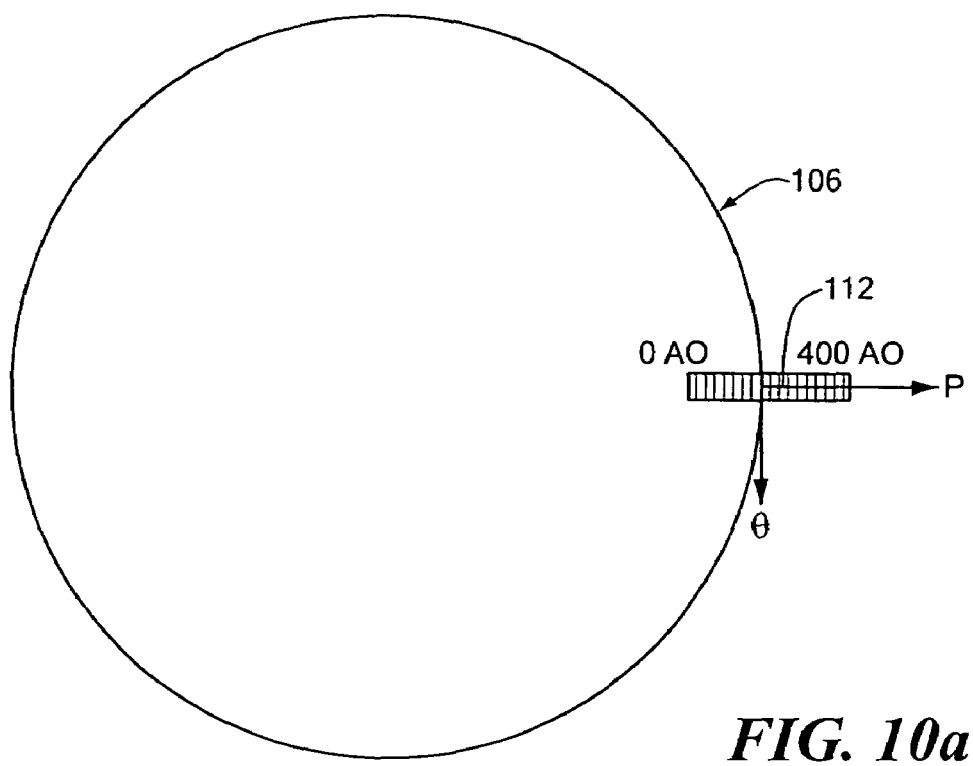
FIGS. 10a-10b are diagrams illustrating the sensitivity of the wafer inspection system of FIG. 1.

In the preferred mode of operation, the wafer inspection system 100 scans the edge 105 of the semiconductor wafer 106 to determine the eccentricity of the placement of the wafer 106 on the theta stage 103. Specifically, the wafer inspection system 100 determines the wafer edge 105 by determining the radius (i.e., the AO position, see FIG. 10a) at which the LC optics 104 detects a loss in the reflected light intensity as the light beam 108 passes over the edge 105. It is noted that a defect in the wafer edge generally causes a loss in the reflected light intensity that deviates from the detected light intensity losses used to determine the wafer edge. The LC optics 104 detects signals indicative of one or more defects in the wafer edge, and the processor 208 determines the locations of the detected edge defects using the counts provided by the encoder. The processor 208 then converts all of the information relating to the detected edge defects and their corresponding locations on the wafer edge to digital form for subsequent processing.

Figure 3:
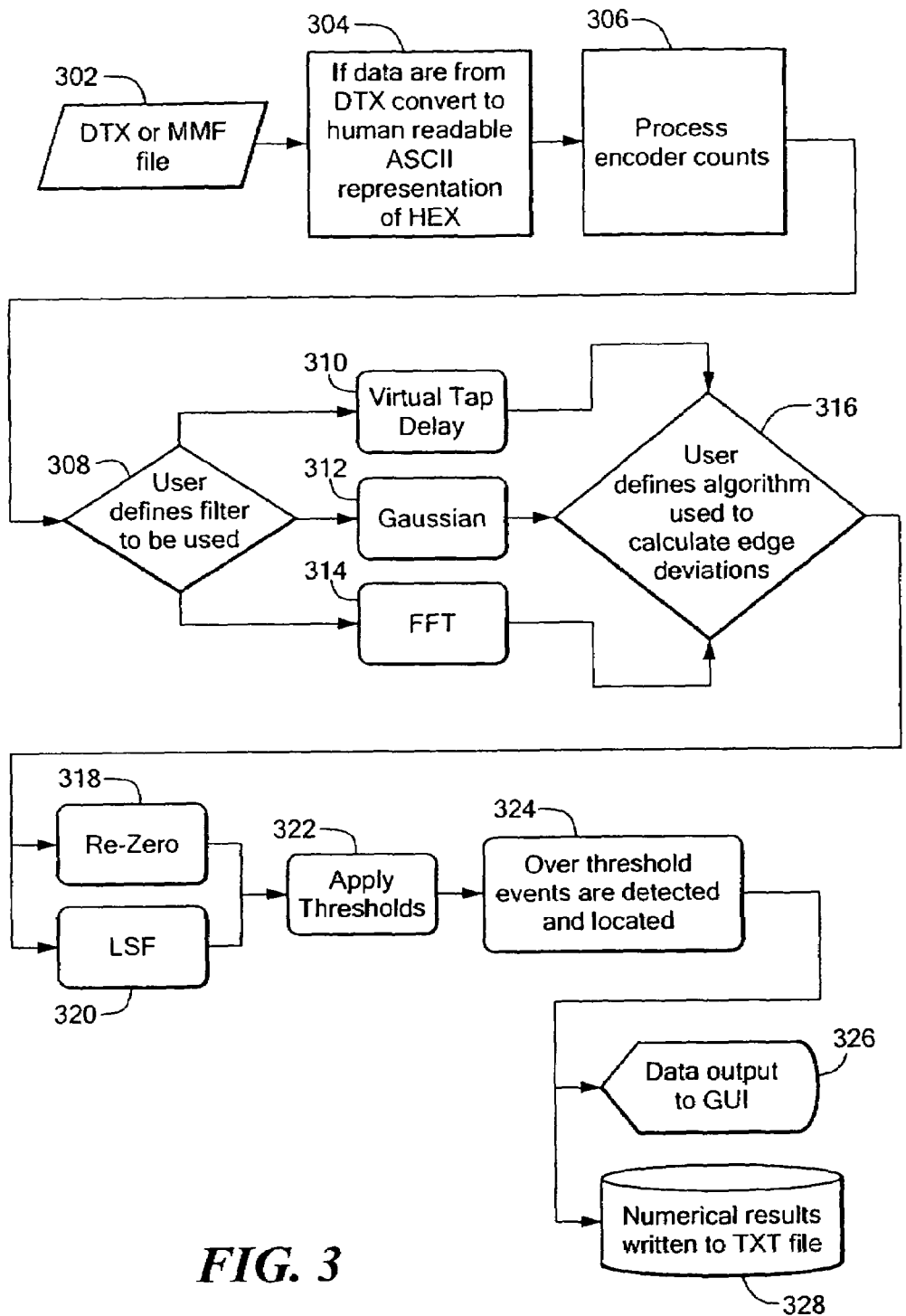
FIG. 3 is a flow diagram illustrating a method of processing data accumulated during the laser beam sweep of the wafer edge depicted in FIG. 1.

FIG. 3 depicts a method of processing the digital data representing the locations of the edge defects in the semiconductor wafer 106 (see FIG. 1). In the presently disclosed embodiment, the data processing steps of FIG. 3 are performed by the processor 208 executing a program out of its associated memory 210 (see FIG. 2). As depicted in step 302, each individual datum is extracted from a Discontinuous Transmission (DTX) file for off-line data processing, or a Memory Mapped File (MMF) containing the raw data for on-line data processing. In the disclosed embodiment, the DTX file comprises a series of hexadecimal data packets. In the event the data are extracted from a DTX file, the data are converted, as depicted in step 304, from the hexadecimal format to a human readable ASCII representation of the hexadecimal data. In step 304, the data are written to active memory. Converting the hexadecimal arrays to a human readable ASCII representation is a convenient way to check data integrity and program progress. Next, the position of the laser spot on the wafer is determined by analyzing the encoder counts provided by the theta stage 103, as depicted in step 306. Specifically, the process maps the data in the storage array to the number of encoder counts and defines the relative position for each datum. In the disclosed embodiment, the system collects data from a little more than one full revolution of the wafer. Because edge defects in a wafer are typically high frequency events, the data are filtered to remove low frequency noise while preserving information relating to the high frequency edge defects. As depicted in step 308, a user of the wafer inspection system selects a suitable filter for filtering the wafer edge data. Typically, the data collected have noise associated with the signal. The system user has the ability to filter data to limit the influence of any noise present. The virtual tap delay filter (see step 310) and the Gaussian filter (see step 312) are intended to reduce noise. The Fast Fourier Transform (FFT) portion (see step 314) is intended to allow the user a rapid way of determining frequencies present in the data.

Figures 4, 5:
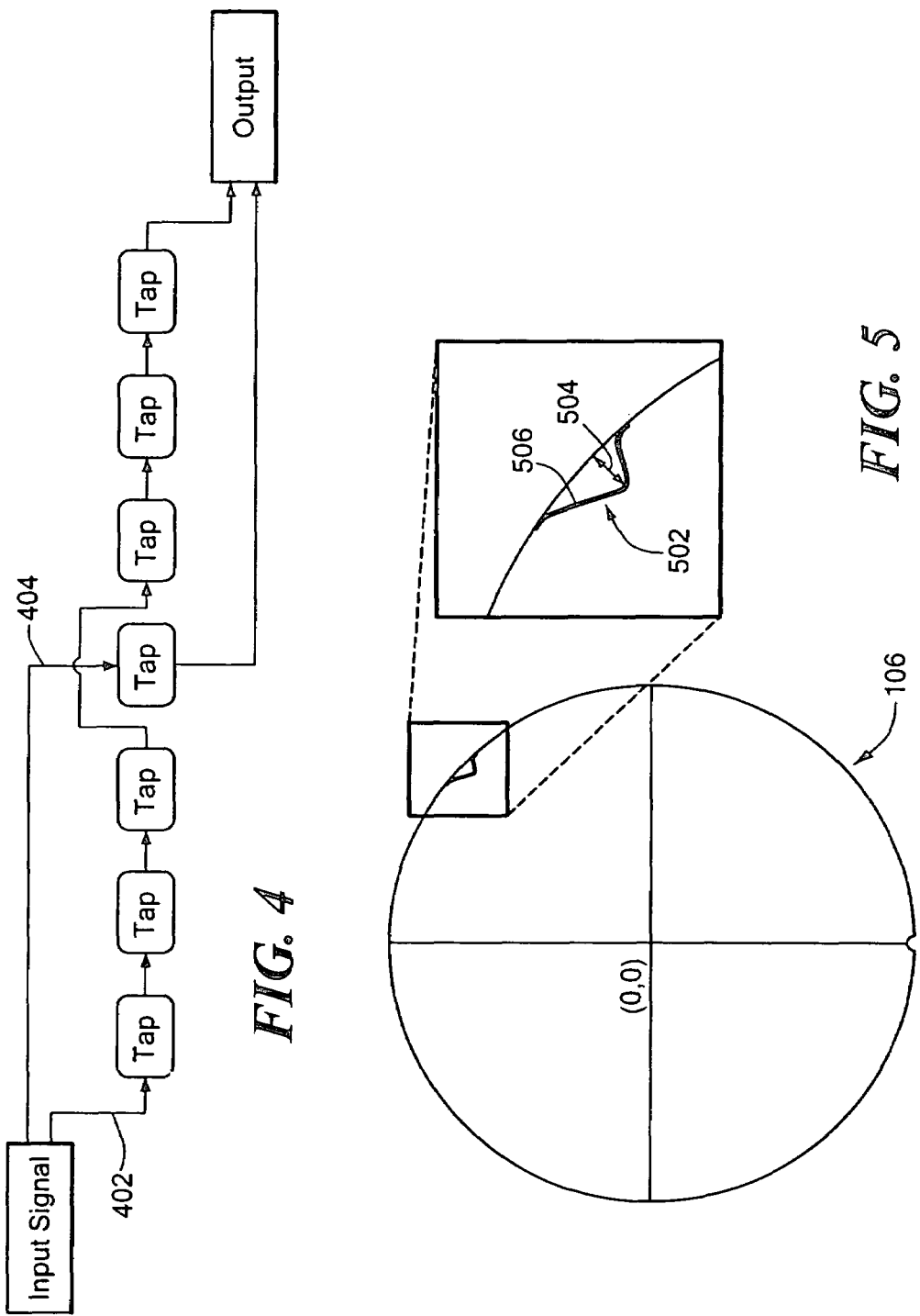
FIG. 4 is a block diagram of a virtual tap delay filter employed in the data processing of FIG. 3.
FIG. 5 is a diagram illustrating the functionality of a first algorithm for characterizing the edge defects detected by the wafer inspection system of FIG. 1.

In the presently disclosed embodiment, the virtual tap delay filter operates like a series of capacitors to induce a lag between a first input signal 402 and a second input signal 404 (see FIG. 4). For example, the induced voltage lag may be determined by the number of capacitors and by the capacitance of each capacitor. Further, as the induced lag increases, the output of the filter becomes smoother. The virtual tap delay filter operates as a high pass filter to reduce the apparent noise in the wafer edge data. Specifically, the filter is operative to remove the low spatial frequency components from the data. Moreover, the virtual tap delay filter provides a weighted average output, in which the average output is weighted towards a central data point of interest.

The Gaussian filter is also operative to reduce the apparent noise in the wafer edge data. Specifically, the Gaussian filter $G(x)$ weights the edge data by the standard deviation $\sigma$ of the data distribution, i.e., $$G(x)=(1/(2\pi\sigma)^{1/2})\exp(x^2/2\sigma^2). \quad (1)$$

The FFT filter is operative to decompose the wafer edge data into its sine and cosine components. Specifically, the FFT filter receives input data from the spatial domain and transforms it to the frequency domain, in which each data point represents a particular frequency included in the spatial domain. As a result, the FFT filter provides the user of the wafer inspection system with an indication of the power spectral density function corresponding to the wafer edge.

Next, the user selects one or more predetermined algorithms for locating edge deviations, as depicted in step 316. In the preferred embodiment, the predetermined algorithms are executed by the processor 208 out of its associated memory 210 (see FIG. 2). At this point, the data have been assembled and noise filtering has been achieved. In order to determine what a deviation is in the data, a baseline has to be established for each data set. The data are either fit to a circle by a least squares fit technique (LSF) (see step 320) or compared to a predefined pixel within each individual scan line, i.e., re-zeroed (see step 318). By referencing higher frequency deviations to the bulk data, a more self-consistent baseline is achieved without introducing error by comparing the data to a template. Next, the edge deviations are applied, as depicted in step 322, to one or more predetermined thresholds. The user can define the permissible amount of variation between each datum and the baseline. The permissible amount of variation is defined as a threshold. In the disclosed embodiment, there are three thresholds available to the user. Two of the thresholds consider the radial or "in scan" behavior of the data. The third threshold considers the tangential or "cross scan" behavior of the data. Each datum is compared to its nearest neighbor data. Over-threshold flagged events are then detected and located on the wafer edge, as depicted in step 324. If a pre-defined number of the nearest neighbor data exceeds the tangential threshold, then these data are flagged as a defect. This information is passed on to be displayed by a human readable display including a suitable graphical user interface (GUI) (see step 326). The user may also elect to have this information written to a text (TXT) file (see step 328). In one embodiment, the flagged event providing the largest deviation from a predetermined threshold is designated as a wafer orientation fiducial notch, and all other over-threshold events are designated as edge defects. It is noted that the location of the fiducial notch may alternatively be determined using stored wafer edge data.

Following the execution of the data processing method of FIG. 3 to determine the locations of defects in the wafer edge, the located wafer edge defects are characterized. In the preferred embodiment, the processor 208 executes one or more predetermined algorithms out of its associated memory 210 (see FIG. 2) to characterize the located edge defects. For example, FIG. 5 illustrates the functionality of a first algorithm in which an edge defect 502 (see detail) on the wafer 106 is characterized by a corresponding magnitude value. Specifically, this first algorithm is operative to convert the light intensity data accumulated by the LC optics 104 (see FIG. 1) over a given arc length into a magnitude value having units of mm. The magnitude value (mm) is indicative of a deviation 504 from the predetermined edge 506 resulting from the edge defect 502.

Figure 6:
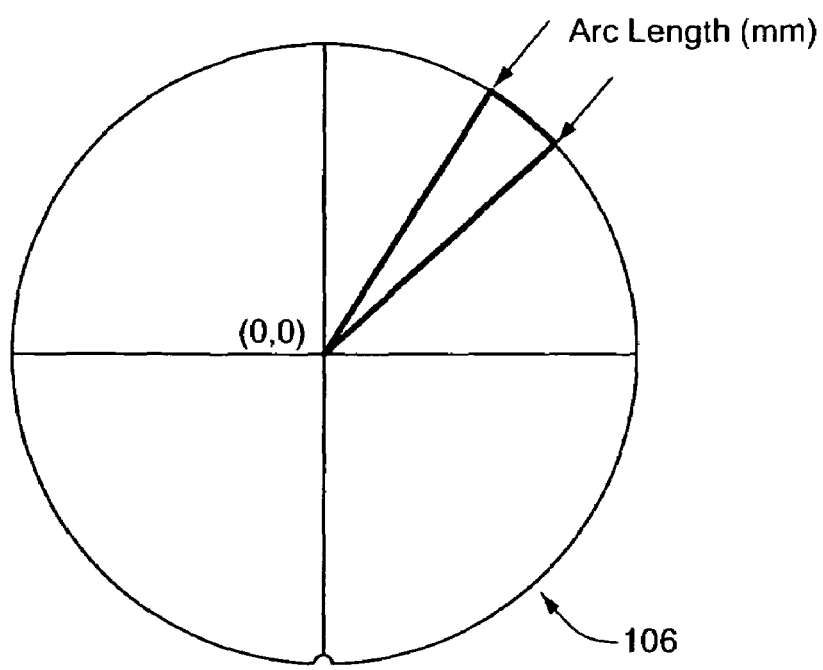
FIG. 6 is a diagram illustrating the functionality of a second algorithm for characterizing the edge defects detected by the wafer inspection system of FIG. 1.
Figure 7:
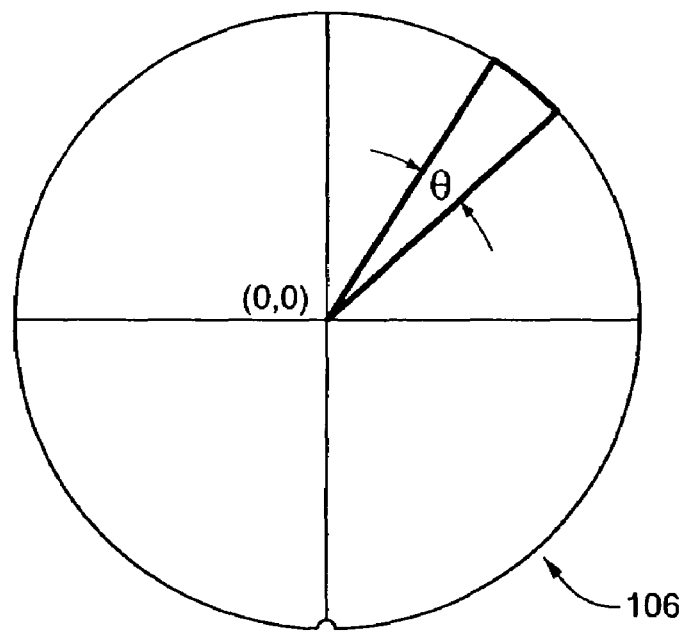
FIG. 7 is a diagram illustrating the functionality of a third algorithm for characterizing the edge defects detected by the wafer inspection system of FIG. 1.

FIG. 6 illustrates the functionality of a second algorithm in which the change in light intensity due to a wafer edge defect is determined over a particular arc length (mm). Specifically, this second algorithm is operative to determine the change in light intensity due to an edge defect along the arc length using the light intensity data accumulated by the LC optics 104 (see FIG. 1). FIG. 7 illustrates the functionality of a third algorithm in which the change in light intensity due to a wafer edge defect is determined with reference to the angle θ subtended by the arc length of FIGS. 5-6.

Figure 8:
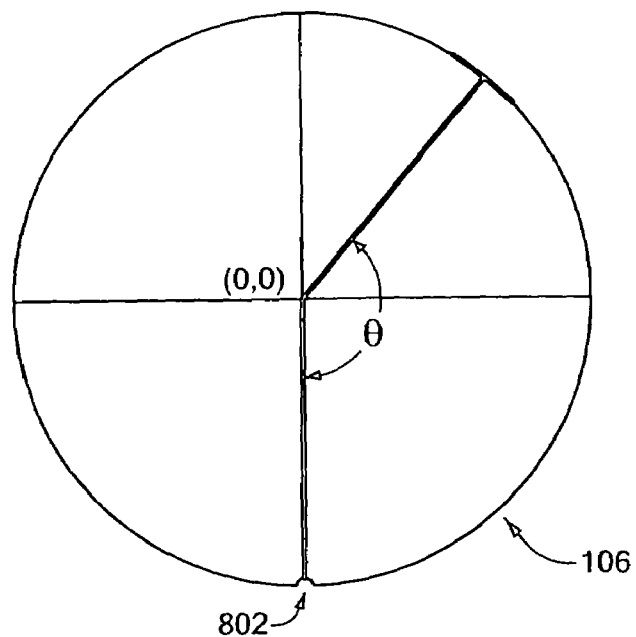
FIG. 8 is a diagram illustrating the functionality of a fourth algorithm for characterizing the edge defects detected by the wafer inspection system of FIG. 1.

FIG. 8 illustrates the functionality of a fourth algorithm in which the angle Θ from the wafer orientation fiducial 802 to the edge defect is determined in degrees. Specifically, this fourth algorithm is operative to determine the angle Θ from the fiducial 802 to the center of the edge defect 502 (see FIG. 5).

Figure 9:
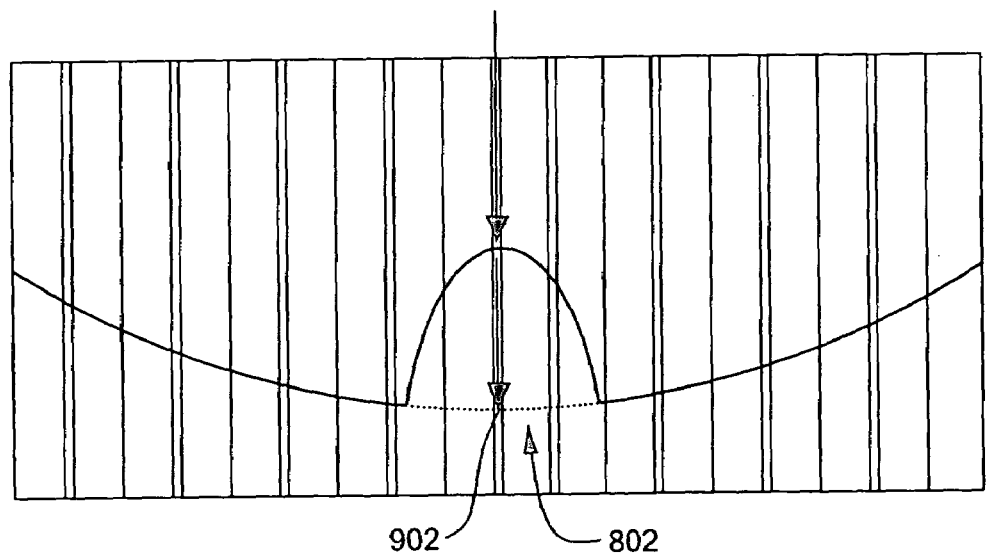
FIG. 9 is a diagram illustrating a method of calibrating the wafer inspection system of FIG. 1.

It should be noted that the wafer orientation fiducial notch may be employed to calibrate the wafer inspection system 100 (see FIG. 1). Specifically, the filtered data corresponding to the wafer region including the fiducial 802 (see the raster display of the wafer region including the fiducial 802 in FIG. 9) is fit to a predetermined notch by a suitable LSF routine, and the maximum deviation of the notch data from the LSF is designated as a calibration point, e.g., the calibration point 902 (see FIG. 9). Next, a calibration factor corresponding to the calibration point 902 is determined and used to calibrate all subsequent wafer edge measurements. In the presently disclosed embodiment, the wafer inspection system 100 (see FIG. 1) employing a rastered, oblique, incident laser and a quadcell photodetector for collecting laser light reflected from the wafer has a sensitivity of about 10 μm in a radial direction ρ and about 26 μm in a tangential direction θ (see FIG. 10a). It should be understood that the sensitivity of the system 100 is limited by the capabilities of the system hardware. In the preferred embodiment, the sensitivity of the system 100 is user-definable based on the characteristics of the wafer edge imperfections that should be considered defects.

Figure 10B:
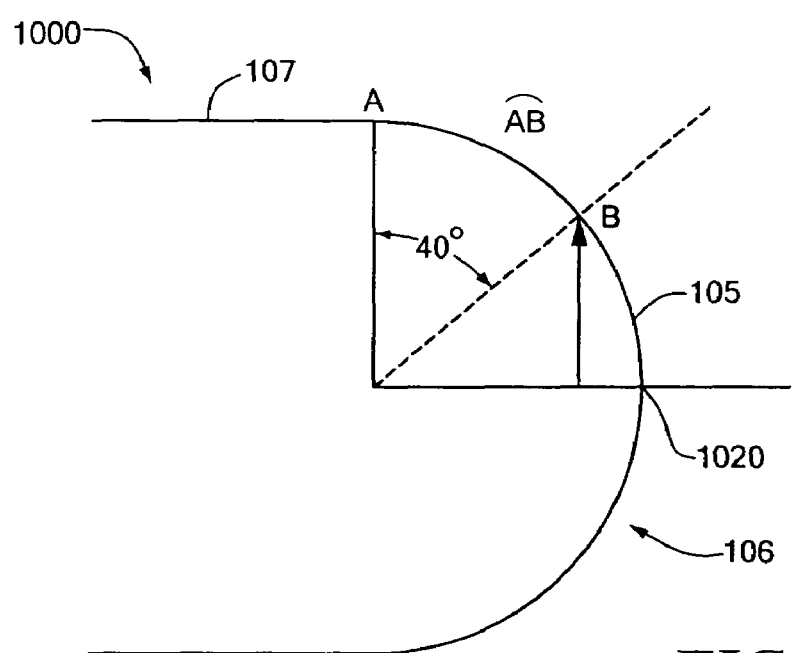

As described above, the wafer inspection system 100 (see FIG. 1) detects the edge 105 of the wafer 106 by determining the point at which the reflected light beam 110 no longer excites the quadcell photodetector of the LC optics 102, i.e., the point at which the detected light drops below a minimum threshold. The system 100 defines the edge 105 of the wafer 106 by this loss of signal intensity. FIG. 10b depicts a cross-sectional profile 1000 of the edge 105 of the wafer 106 (see also FIG. 10a). In the illustrated embodiment, the system 100 does not detect edge defects out to the wafer's crown 1020 due to the slope of the edge profile 1000. The region of maximum sensitivity along the scanned edge profile 1000 may be determined by scribing the edge 105 of the wafer 106. For example, a number of scribe marks (not shown) representing respective wafer edge defects may be made at various locations on the wafer edge 105. In the presently disclosed embodiment, the majority of the scribe marks detected by the system 100 are located on the wafer edge 105 between point A on the wafer surface 107 and point B, defining an angle of about 40° down from the wafer surface on the edge bevel (see FIG. 10b). This 40° angle represents the slope limitation of the presently disclosed system 100.

It is noted that the performance of the wafer inspection system 100 may be enhanced at least in part by suitable modifications to the rastered, oblique, incident laser and/or the quadcell photodetector for collecting the reflected laser light. Moreover, in the event an edge defect exists beyond the slope limitation defined above, the wafer inspection system 100 may be able to detect the defect if it generates sufficient distortion in the specularly reflected laser beam. It should also be understood that additional edge defects disposed beyond the slope limitation of the system 100 may be detected by inverting the wafer 106 and by inspecting the wafer from the backside.

The presently disclosed semiconductor wafer edge scanning inspection system 100 (see FIG. 1) may be better understood by reference to the following illustrative examples. In a first example, the wafer inspection system 100 determines the radial and tangential dimensional positions of a focused laser spot on the wafer 106. For example, the focused laser spot may be projected onto the wafer 106 by the AOD 102 (see FIG. 1). The system 100 determines the radial position of the laser spot with respect to the wafer 106 by tracking the frequency output of a radio frequency (RF) generator driving a piezoelectric crystal included in the AOD 102, and by comparing this frequency with the elapsed time. Next, the frequency/time data set is built. Pixel data are then constructed by suitable data processing within the wafer inspection system 100 as the AOD electronics refresh, and the data buffers are purged.

Accordingly, in the presently disclosed embodiment, the refresh rate of the AOD electronics is used to determine the radial dimension corresponding to each pixel. Further, the edge of the wafer is determined by summing the pixels populated with light channel responses. In the disclosed embodiment, data are actively collected over about 400 pixels. Next, the wafer inspection system 100 determines the tangential dimension of the laser spot with respect to the wafer 106 by tracking the encoder counts provided by the theta stage 103. The laser spot location is then determined by the radial and tangential dimensional components ρ,θ.

Figure 11:
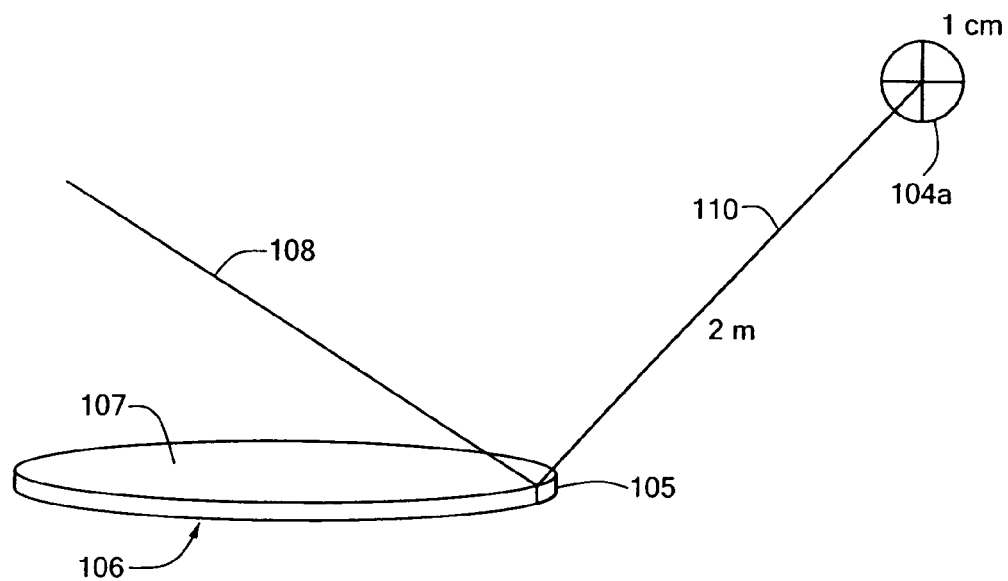
FIG. 11 is a diagram illustrating a first illustrative example of using the wafer inspection system of FIG. 1.

A second example illustrates a determination of when the LC optics 104 (see FIG. 1) detects a deflection of the reflected laser light. As described above, the LC optics 104 may include a quadcell photodetector 104a (see FIG. 11), which typically includes a circular piece of silicon about 1 cm in diameter. As shown in FIG. 11, the quadcell photodetector 104a is divided into four quadrants of equal size. The gap between these quadrants is about 30 μm, which is approximately equal to the laser beam's diameter at $1/e^2$. The LC optics 104 are configured so that the laser is focused in the center of the crosshairs formed by the four quadrants when the slope of the wafer surface is zero. When the slope of the wafer surface deviates from zero, the resulting deflection of the laser on the quadcell photodetector 104a produces a voltage due to the photoelectric effect. The direction and magnitude of the laser's deflection are calculated by determining the changes in the ratio of this voltage relative to the four quadrants of the quadcell. When the sum of the voltages of the four quadrants falls below a predetermined threshold, the laser is considered to have left the wafer. In this way, the wafer inspection system 100 may be used to locate and to inspect the edge 105 of the wafer 106.

A third example illustrates the determination of an edge defect. FIG. 11 depicts the wafer edge 105, which comprises a circular bevel. In this example, the edge 105 of the wafer 106 is defined by the pixels containing no data that are the greatest distance from the center of the wafer. It is noted that the wafer inspection system 100 constructs pixels containing no data when the focused spot produced by the incident laser beam 108 leaves the surface/edge of the wafer. As described in greater detail below, the laser spot will not be detectable in this illustrative example when the slope α of the wafer surface 107 exceeds about 1.25 mrad, i.e., $$\alpha_{max} = \frac{1}{2}(0.005/2) = 1.25 \text{ mrad} \quad (2)$$

Figure 12:
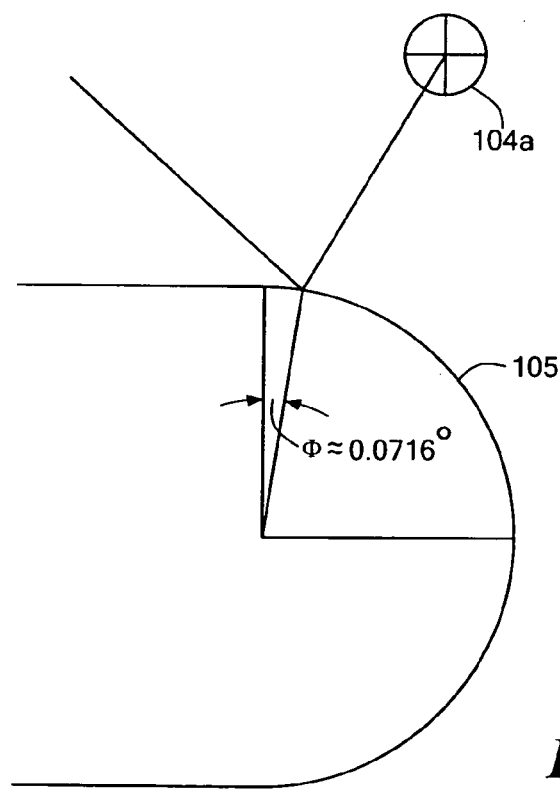
FIG. 12 is a diagram illustrating the angular response of the wafer inspection system employed in the first example of FIG. 11.

(see also FIG. 11), in which "0.005" m is an exemplary deflection of the laser spot on the quadcell photodetector, and "2" m is an exemplary distance from the wafer to the quadcell. As a result, the edge 105 of the wafer 106 is about 0.0716° from where the polished wafer surface meets the edge, i.e., $$\phi = 180(1.25/\pi) \approx 0.0716°, \quad (3)$$

as illustrated in FIG. 12. It should be understood that the analysis performed in this third example is based on an idealized edge profile comprising a half circle. Analysis results may vary based on the specific characteristics of a given wafer edge profile.

Figure 13B:
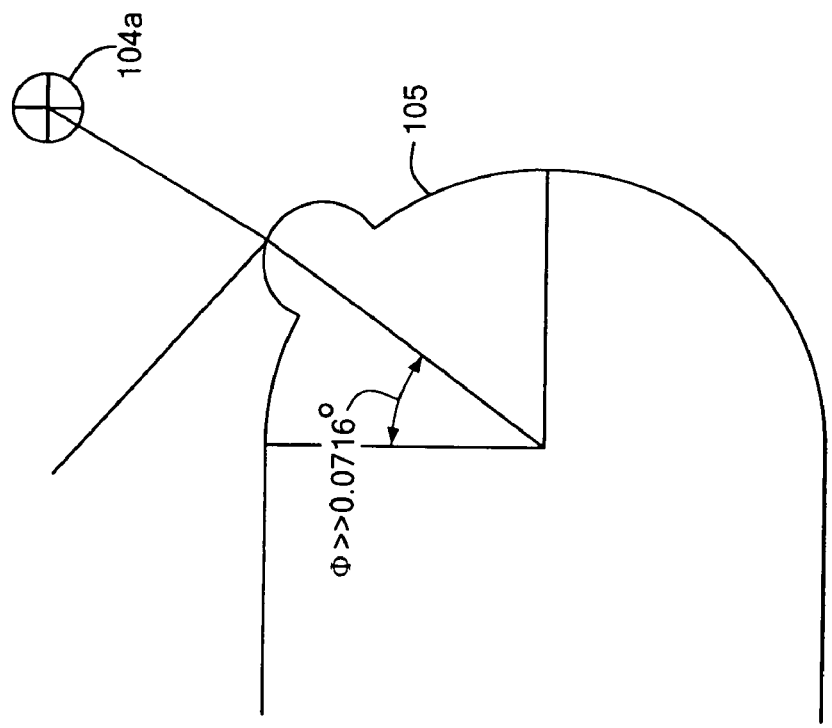
FIGS. 13a-13b are diagrams illustrating detected edge defects into and out of a surface of an edge profile, the edge defects being detected in the first example of FIG. 11.
Figure 13A:
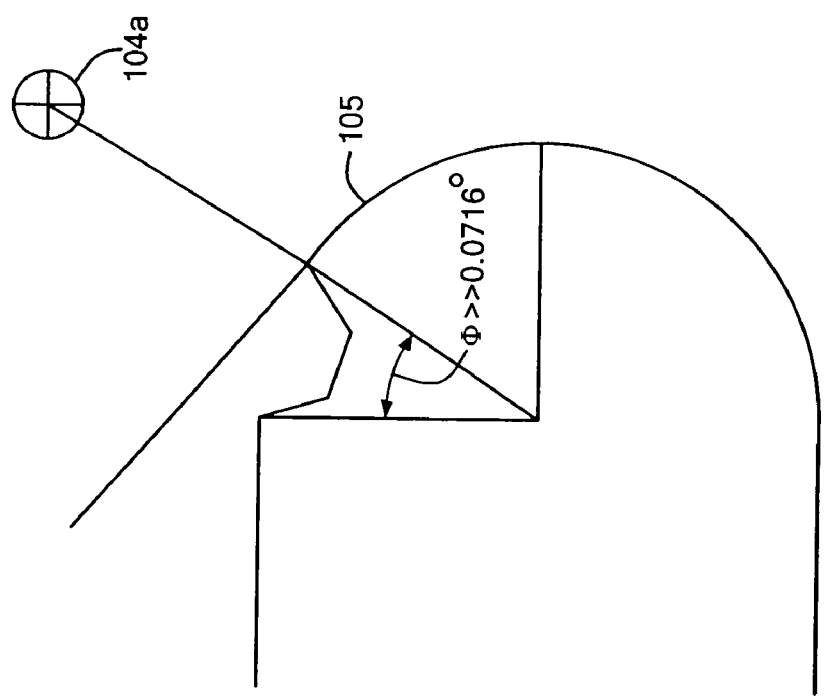

It is appreciated that when a defect exists on a wafer edge, the irregularity of the edge defect typically causes specular distortions in the reflected laser beam. Such defects may be formed into the surface of the edge profile (see FIG. 13a), or may protrude from the edge profile surface (see FIG. 13b). In both cases, the responses collected by the quadcell photodetector 104a may comprise one or a series of signal intensity loss indications. When the collected response comprises a series of signal losses, the last pixel in the series to record a loss of signal (i.e., no pixel data) defines the wafer edge.

In a fourth example, the wafer inspection system 100 assembles the accumulated pixel data at the conclusion of each edge scan. The system 100 then takes the positional information for each theta stage encoder count and builds a map of the wafer edge. Next, the map is fit to an optimal circular wafer edge by a suitable LSF routine. Predetermined thresholds are then applied. When an edge defect causes a variation from the optimal circle by an amount greater than the predetermined threshold, the system 100 records the defect location for subsequent analysis.

Figure 14:
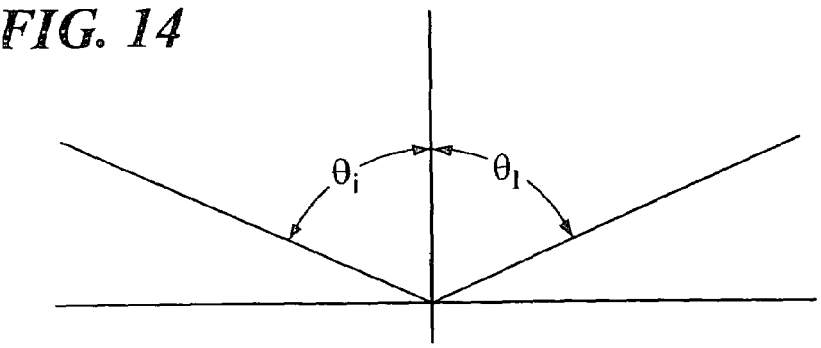
FIG. 14 is a diagram illustrating the law of reflection in a second illustrative example of using the wafer inspection system of FIG. 1, in which the wafer surface has a slope equal to zero.
Figure 15:
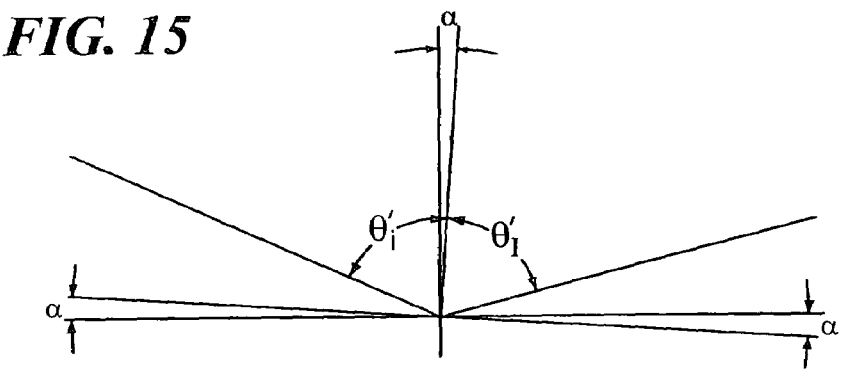
FIG. 15 is a diagram illustrating the law of reflection in the second illustrative example of FIG. 14, in which the wafer surface has a non-zero slope.

It should be appreciated that there is an angular dependence between the slope of the wafer surface 107 and shifts in the angle of the reflected laser beam 110 (see also FIG. 1). FIG. 14 depicts the known law of reflection, in which the angle of incidence $\theta i$ equals the angle of reflection $\theta I$. As shown in FIG. 15, when a change in slope is introduced, the law of reflection still holds, i.e., $\theta'_i = \theta'_I$.

Figure 16:
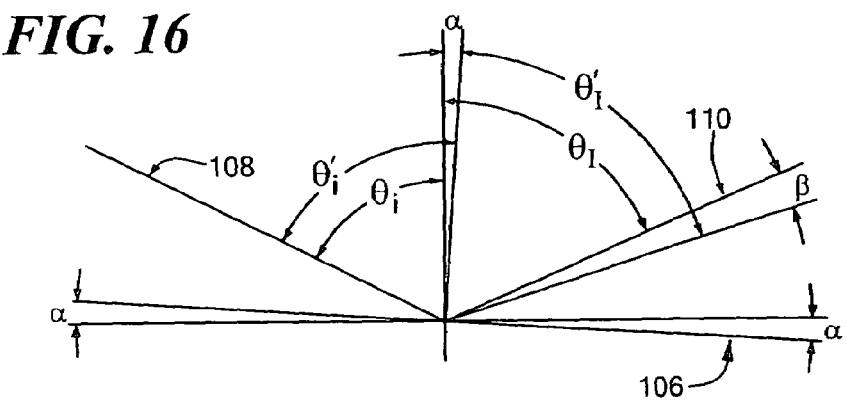
FIG. 16 is a diagram illustrating a determination of the angular change in the wafer surface slope in the second illustrative example of FIG. 14.

It is noted that deviations in the angle of reflection $\theta'_I$ are primarily due to a change in the slope $\alpha$ of the surface 107 of the wafer under inspection. As depicted in FIG. 16, the slope $\alpha$ of the wafer surface 107 may be expressed as $$\theta'_i - \theta_i = \alpha \quad (4)$$

$$\theta'_I - \theta_I = \alpha. \quad (5)$$

The angle $\beta$ represents a change in the angle of the reflected laser beam 110. Such angular changes $\beta$ may be determined as follows, $$\beta = \theta'_I + \theta'_i - \theta_I - \theta_i, \text{ or} \quad (6)$$

$$\beta = \theta'_I - \theta_I + \theta'_i - \theta_i. \quad (7)$$

Accordingly, after substituting equations (4) and (5) into equation (7), $$\beta = 2\alpha. \quad (8)$$

Next, the magnitude of the slope $\alpha$ of the wafer surface 107 that causes the reflected laser beam 110 to leave the quadcell photodetector (i.e., $\alpha_{max}$; see also equation (2) above) is determined as follows. It is first noted that the amount of deflection of the laser spot on the quadcell photodetector is equal to the distance from the wafer 106 to the quadcell times the tangent of the angle $\beta$, i.e., (Deflection on quadcell)=(Distance from wafer to quadcell)tan $\beta$ \quad (9)

In this analysis, $\beta$ is small enough to allow use of the small angle approximation, i.e., $$\tan \beta = \beta. \quad (10)$$

It follows that (Deflection on quadcell)=(Distance from wafer to quadcell)$\beta$, \quad (11)

(Deflection on quadcell)=(Distance from wafer to quadcell)$2\alpha_{max}$, \quad (12)

$$\alpha_{max} = \frac{1}{2} \frac{\text{(Deflection on quadcell)}}{\text{(Distance from wafer to quadcell)}}, \quad (13)$$

$$\alpha_{max} = (\tfrac{1}{2})(0.005/2) = 1.25 \text{ mrad}. \quad (14)$$

Figure 17:
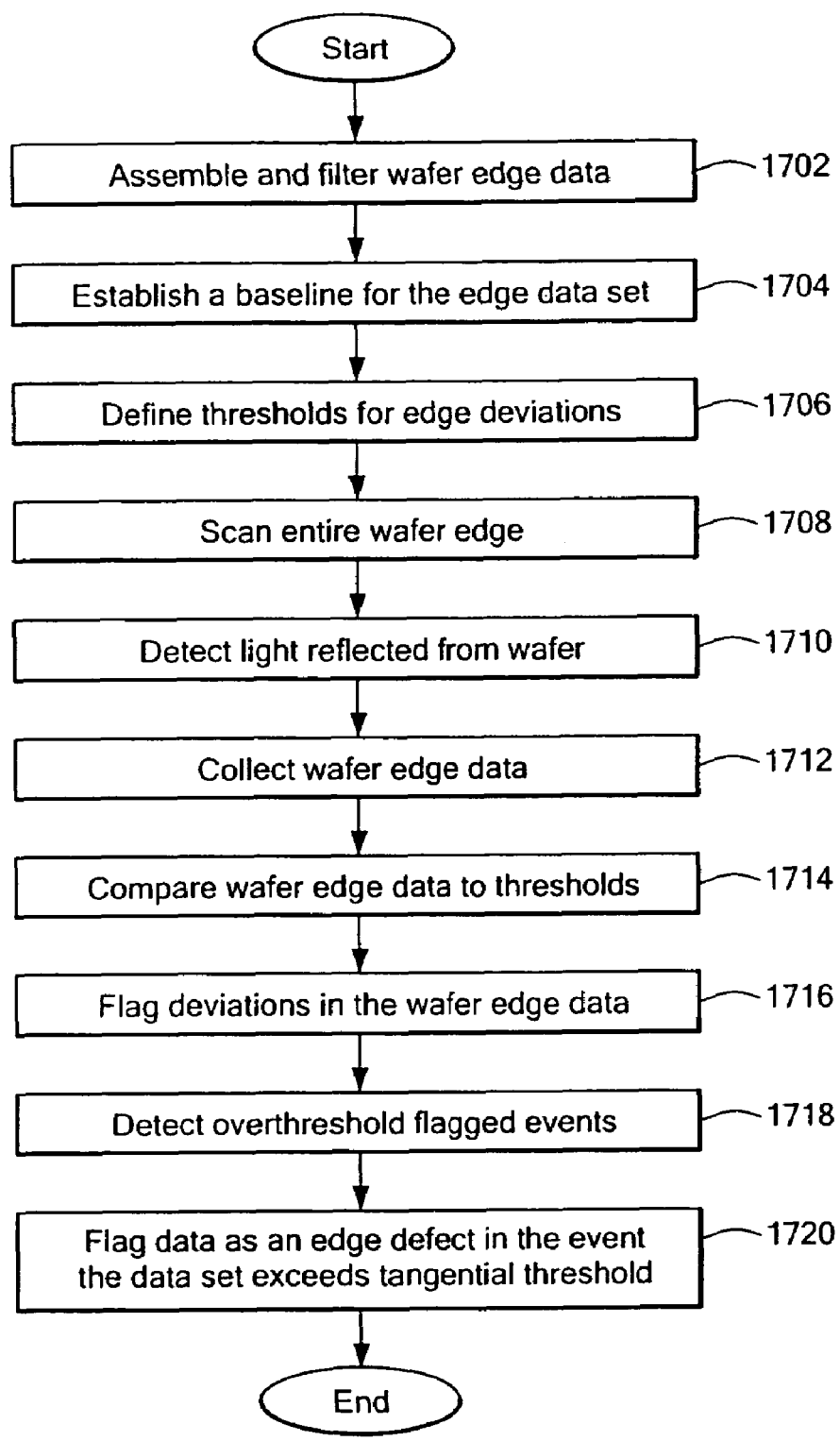
FIG. 17 is a flow diagram of a method of operating the wafer inspection system of FIG. 1.

A method of operating the presently disclosed semiconductor wafer edge scanning inspection system 100 is illustrated by reference to FIG. 17. As depicted in step 1702, wafer edge data are assembled and filtered. The wafer edge data include edge data representing the locations of a plurality of wafer edge defects. A baseline is then established for the data set, as depicted in step 1704, using a suitable LSF or re-zeroing technique. Next, radial and tangential thresholds for edge deviations are defined, as depicted in step 1706, based on a predetermined permissible amount of variation between each datum and the baseline. The entire wafer edge is then scanned, as depicted in step 1708, and light reflected from the wafer is detected, as depicted in step 1710, to determine the intensity loss. Next, wafer edge data are collected, as depicted in step 1712, based on the light intensity losses detected in step 1710. The wafer edge data are then compared, as depicted in step 1714, to the thresholds defined in step 1706. Next, deviations in the edge data (i.e., over-threshold events) are flagged, as depicted in step 1716. Over-threshold flagged events are then detected and located, as depicted in step 1718, on the wafer edge. Finally, in the event the data set exceeds the tangential threshold, the data are flagged as an edge defect, as depicted in step 1720.

It will further be appreciated by those of ordinary skill in the art that modifications to and variations of the above-described system and method of detecting a wafer edge using collimated light may be made without departing from the inventive concepts disclosed herein. Accordingly, the invention should not be viewed as limited except as by the scope and spirit of the appended claims.

What is claimed is:

1. A system for inspecting an edge of a semiconductor wafer, comprising:

a light source configured to project at least one first beam of light at a predetermined angle relative to a surface of the semiconductor wafer, the first light beam being projected to scan at least a portion of the wafer edge, thereby producing at least one second beam of light reflected from the wafer edge;

a light detector configured to detect the second light beam reflected from the wafer edge; and a processor operative:

to convert the detected second light beam to actual edge data representative of the scanned wafer edge portion, the scanned wafer edge portion having radial and tangential dimensions, the actual edge data includin actual edge datum points disposed in the radial dimension and actual edge datum points disposed in the tangential dimension;

to determine at least one radial threshold for use in at least one comparison of nearest neighboring datum points disposed in the radial dimension of the scanned wafer edge portion; to deternine at least one tangential threshold for use in at least one comparison of nearest neighboring datum points disposed in the tangential dimension of the scanned wafer edge portion;

to compare at least two nearest neighboring datum points disposed in the radial dimens ion to obtain first nearest neighbor comparison data, and to compare the first nearest neighbor comparison data to the at least one radial threshold to detect the wafer edge;

to compare at least two nearest neighboring datum points disposed in the tangential dimension to obtain second nearest neighbor comparison data, and to compare the second nearest neighbor comparison data to the at least one tangential threshold; and in the event the second nearest neighbor comparison data exceeds the at least one tangential threshold, to designate the at least two nearest neighboring datum points disposed in the tangential dimension as corresponding to a wafer edge defect.

2. The system of claim 1 wherein the processor is further operative to locate the wafer edge defect on the wafer edge.

3. The system of claim 1 wherein the predetermined angle is an oblique angle.

4. The system of claim 1 wherein the first light beam is projected to scan the wafer edge in its entirety, and the processor is operative to accumulate edge data representative of the entire wafer edge.

5. The system of claim 1 wherein the processor is operative to filter the actual edge data to remove low frequency data components.

6. The system of claim 5 wherein the processor is operative to filter the actual edge data using a filter selected from a tap delay filter and a Gaussian filter.

7. The system of claim 1 wherein the processor is operative to determine at least one of the at least one radial threshold or at least one of the at least one tangential threshold by establishing a baseline for the edge data in the respective radial and tangential dimensions, and by determining the respective threshold based on a permissible amount of variation between the edge data and the baseline.

8. The system of claim 7 wherein the processor is operative to establish the baseline by fitting the actual edge data to a circle by a least squares fit (LSF) technique.

9. The system of claim 1 wherein the processor is operative to execute at least one algorithm for characterizing the wafer edge defect.

10. The system of claim 9 wherein the processor is operative to execute the algorithm to characterize the edge defect by a corresponding magnitude value.

11. The system of claim 9 wherein the processor is operative to execute the algorithm to convert light intensity data over an arc length corresponding to the scanned edge portion into a magnitude value, the magnitude value being indicative of a deviation of the wafer edge from a predetermined edge profile.

12. The system of claim 11 wherein the processor is operative to execute the algorithm to determine the arc length corresponding to the scanned edge portion, and to determine an angle subtended by the determined arc length.

13. The system of claim 9 wherein the processor is operative to execute the algorithm to convert light intensity data over an arc length corresponding to an edge portion disposed between a wafer orientation fiducial notch and the edge defect into a magnitude value, the magnitude value being indicative of a deviation of the wafer edge from a predetermined edge profile.

14. The system of claim 13 wherein the processor is operative to execute the algorithm to determine the arc length corresponding to the edge portion disposed between the wafer orientation fiducial notch and the edge defect, and to determine an angle subtended by the determined arc length.

15. The system of claim 1 further including a wafer handling device configured to hold the wafer during inspection.

16. The system of claim 15 wherein the wafer handling device is configured to rotate and to translate the wafer during inspection, thereby allowing the first light beam to generate a substantially spiral pattern of light while scanning the wafer edge.

17. The system of claim 16 wherein the wafer handling device includes an encoder configured to provide an indication of a rotational position of the device.

18. The system of claim 1 wherein the first light beam comprises a collimated beam of laser light.

19. The system of claim 1 wherein the light source comprises an acousto-optic deflector.

20. The system of claim 1 wherein the light detector comprises a quadcell photodetector.

21. The system of claim 1 wherein the slope of the wafer surface is equal to $\alpha$, wherein a change in an angle of the second light beam relative to the wafer surface is equal to $\beta$, and $\beta=2\alpha$.

22. A method of inspecting an edge of a semiconductor wafer, comprising the steps of:
projecting, by a light source, at least one first beam of light at a predetermined angle relative to a surface of the semiconductor wafer, the first light beam being projected to scan at least a portion of the wafer edge, thereby producing at least one second beam of light reflected from the wafer edge;
detecting, by a light detector, the second light beam reflected from the wafer edge;
converting, by a processor, the detected second light beam to actual edge data representative of the scanned wafer edge portion, the scanned wafer edge portion having radial and tangential dimensions, the actual edge data including actual edge datum points disposed in the radial dimension and actual edge datum points disposed in the tangential dimension;
determining at least one radial threshold for use in at least one comparison of nearest neighboring datum points disposed in the radial dimension of the scanned wafer edge portion;
determining at least one tangential threshold for use in at least one comparison of nearest neighboring datum points disposed in the tangential dimension of the scanned wafer edge portion;
comparing, by the processor, at least two nearest neighboring datum points disposed in the radial dimension to obtain first nearest neighbor comparison data, and comparing the first nearest neighbor comparison data to the at least one radial threshold to detect the wafer edge;
comparing, by the processor, at least two nearest neighboring datum points disposed in the tangential dimension to obtain second nearest neighbor comparison data, and comparing the second nearest neighbor comparison data to the at least one tangential threshold;
in the event the second nearest neighbor comparison data exceeds the at least one tangential threshold, designating the at least two nearest neighboring datum points disposed in the tangential dimension as corresponding to a wafer edge defect; and
storing data indicative of the datum points designated as corresponding to the wafer edge defect in memory.

23. The method of claim 22 further including the step of locating the wafer edge defect on the wafer edge.

24. The method of claim 22 wherein the predetermined angle is an oblique angle.

25. The method of claim 22 wherein the first light beam is projected to scan the wafer edge in its entirety, and further including the step of accumulating edge data representative of the entire wafer edge.

26. The method of claim 22 further including the step of filtering the actual edge data to remove low frequency data components by the processor.

27. The method of claim 26 further including the step of filtering the actual edge data using a filter selected from a tap delay filter and a Gaussian filter.

28. The method of claim 22 further including the steps of establishing a baseline for the edge data, and determining at least one of the at least one radial threshold or at least one of the at least one tangential threshold based on a permissible amount of variation between the data and the baseline by the processor.

29. The method of claim 28 wherein the establishing step includes establishing the baseline by fitting the actual edge data to a circle by a least squares fit (LSF) technique.

30. The method of claim 22 further including the step of executing at least, one algorithm for characterizing the wafer edge defect by the processor.

31. The method of claim 30 wherein the executing step includes executing the algorithm to characterize the edge defect by a corresponding magnitude value.

32. The method of claim 30 wherein the executing step includes executing the algorithm to convert light intensity data over an arc length corresponding to the scanned edge portion into a magnitude value, the magnitude value being indicative of a deviation of the wafer edge from a predetermined edge profile.

33. The method of claim 32 wherein the executing step includes executing the algorithm to determine the arc length corresponding to the scanned edge portion, and to determine an angle subtended by the determined arc length.

34. The method of claim 30 wherein the executing step includes executing the algorithm to convert light intensity data over an arc length corresponding to an edge portion disposed between a wafer orientation fiducial notch and the edge defect into a magnitude value, the magnitude value being indicative of a deviation of the wafer edge from a predetermined edge profile.

35. The method of claim 34 wherein the executing step includes executing the algorithm to determine the arc length corresponding to the edge portion disposed between the wafer orientation fiducial notch and the edge defect, and to determine an angle subLended by the determined arc length.

36. The method of claim 22 further including the step of rotating and translating the wafer during inspection by a wafer handling device, thereby allowing the first light beam to generate a substantially spiral pattern of light while scanning the wafer edge.

37. The method of claim 36 wherein the wafer handling device includes an encoder configured to provide an indication of a rotational position of the device.

* * * * *